United States Patent [19]

Bushell

[11] Patent Number: 4,831,047

[45] Date of Patent: May 16, 1989

[54] TETRAZOLYL COMPOUNDS AND INSECTICIDAL USE THEREOF

[75] Inventor: Michael J. Bushell, Wokingham, England

[73] Assignee: Imperial Chemical Industries PLC, London, England

[21] Appl. No.: 776,907

[22] Filed: Sep. 17, 1985

[30] Foreign Application Priority Data

Oct. 4, 1984 [GB] United Kingdom ............... 8425105
Mar. 29, 1985 [GB] United Kingdom ............... 8508297

[51] Int. Cl.$^4$ .................... C07D 257/04; A61K 31/41
[52] U.S. Cl. ..................................... 514/381; 548/252
[58] Field of Search ............... 514/381, 383; 548/252; 568/809

[56] References Cited

U.S. PATENT DOCUMENTS 3,123,615  3/1964  Rorig ................. 548/252

FOREIGN PATENT DOCUMENTS 0102559  8/1983  European Pat. Off. .
0101288  2/1984  European Pat. Off. ............ 548/250
2153772  5/1973  France .
0043274  4/1981  Japan ................. 548/252
0172904  9/1985  Japan ................. 514/383
1353699  2/1972  United Kingdom .

OTHER PUBLICATIONS

Hamada et al., Chem. Abstr. 48, 9332, (1954).

Primary Examiner—David B. Springer
Attorney, Agent, or Firm—Cushman, Darby & Cushman

[57] ABSTRACT

A compound of formula:

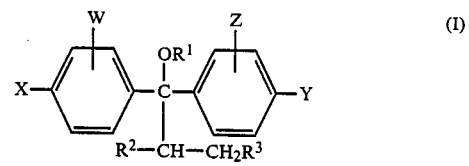

wherein X and Y are each selected from halo, alkyl of up to four carbon atoms, haloalkyl of up to four carbon atoms, alkoxy of up to four carbon atoms, haloalkoxy of up to four carbon atoms, provided that no more than one of X and Y is alkyl or alkoxy, and W and Z are each selected from hydrogen and halogen, $R^1$ is hydrogen, alkyl of up to 6 carbon atoms or carboxylic acyl of up to 10 carbon atoms, $R^2$ is the 1H-tetrazol-1-yl or 2H-tetrazol-2-yl group and $R^3$ is hydrogen or alkyl of up to four carbon atoms. These compounds are useful as pesticides. Intermediates for preparing these compounds are also disclosed.

8 Claims, No Drawings

TETRAZOLYL COMPOUNDS AND INSECTICIDAL USE THEREOF

This invention relates to novel tetrazole derivatives, to methods for their preparation, to insecticidal compositions comprising them, to methods of combating pests using them, and to novel intermediates useful for preparing them.

Various triazole derivatives, for example those of British patent specification No. 1529818, have been proposed as active ingredients for agricultural fungicides. Such compounds do not possess any useful insecticidal properties. We have now discovered that certain tetrazole derivatives have exceptionally useful activity as insecticides.

Accordingly the present invention provides compounds of formula:

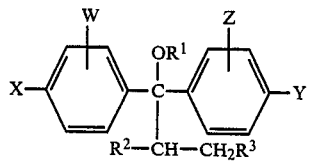

wherein X and Y are each selected from halo, alkyl of up to four carbon atoms, haloalkyl of up to four carbon atoms, alkoxy of up to four carbon atoms, haloalkoxy of up to four carbon atoms, and haloalkenyloxy of up to four carbon atoms, provided that no more than one of X and Y is alkyl or alkoxy, and W and Z are each selected from hydrogen and halogen, $R^1$ is hydrogen, alkyl of up to 6 carbon atoms or carboxylic acyl of up to 10 carbon atoms, $R^2$ is the 1H-tetrazol-1-yl or 2H-tetrazol-2-yl group and $R^3$ is hydrogen or alkyl of up to four carbon atoms.

Preferably X and Y are selected from halo, difluoromethyl, trifluoromethyl, difluoromethoxy, trifluoromethoxy, and W and Z are both hydrogen. $R^2$ is preferably the 2H-tetrazol-2-yl group and $R^1$ and $R^3$ are preferably hydrogen. Particular compounds according to the invention include those set out in Table I wherein the meanings of W, X, Y, Z, $R^1$, $R^2$ and $R^3$ are given for each compound together with a physical characteristic. In the Table "2-T" indicates the 2H-tetrazol-2-yl group and "1-T" indicates the 1H-tetrazol-1-yl group. Where X and Y are the same and W and Z are the same the compound is in the racemic form; where X and Y are not the same the compound is in the form of a diastereomeric mixture.

TABLE I

| Compound No. | W | X | Y | Z | $R^1$ | $R^2$ | $R^3$ | Physical Characteristic |
|---|---|---|---|---|---|---|---|---|
| I | H | F | F | H | H | 2-T | H | mp. 93–95° C. |
| II | 3-F | F | F | 3-F | H | 2-T | H | glass |
| III | H | Cl | Cl | H | H | 2-T | H | oil |
| IV | H | Br | Br | H | H | 2-T | H | mp. 134–137° C. |
| V | H | Cl | CF$_3$ | H | H | 2-T | H | mp. 123–125° C. |
| VI | H | CF$_3$ | CF$_3$ | H | H | 1-T | H | — |
| VII | H | CF$_3$ | CF$_3$ | H | H | 2-T | H | mp. 90–93° C. |
| VIII | H | OCF$_3$ | Cl | H | H | 2-T | H | mp. 104–106° C. |
| IX | H | OCF$_3$ | OCF$_3$ | H | H | 2-T | H | mp. 68–70° C. |
| X | H | OCF$_3$ | OCF$_3$ | H | CH$_3$ | 2-T | H | oil |
| XI | H | OCF$_3$ | OCF$_3$ | H | C$_2$H$_5$ | 2-T | H | — |
| XII | H | OCF$_3$ | OCF$_3$ | H | COCH$_3$ | 2-T | H | oil |
| XIII | H | OCF$_3$ | OCF$_3$ | H | H | 2-T | CH$_3$ | oil |
| XIV | H | OCHF$_2$ | OCHF$_2$ | H | H | 2-T | H | oil |
| XV | H | OCF$_2$CHF$_2$ | OCF$_2$CHF$_2$ | H | H | 2-T | H | oil |
| XVI | H | OCF$_2$CHF$_2$ | OCF=CF$_2$ | H | H | 2-T | H | oil |
| XVII | H | OC$_2$H$_5$ | OCF$_3$ | H | H | 2-T | H | oil |

Especially preferred compounds according to the invention include the following:

1,1-bis(4-trifluoromethylphenyl)-2-(2H-tetrazol-2-yl)propanol (Compound VII),
1,1-bis(4-trifluoromethoxyphenyl)-2-(2H-tetrazol-2-yl)propanol (Compound IX), It will be appreciated that since the compounds of formula I contain at least one chiral centre (the carbon atom bearing the methyl group) and will contain two chiral centres when X is not the same as Y or when Z is not hydrogen, there exists the possibility of different isomeric and diastereoisomeric forms of the compounds. The invention includes within its scope all such isomers in isolation and mixtures thereof including racemic mixtures.

The compounds of formula I wherein $R^1$ is hydrogen may be prepared by a variety of processes such as those illustrated in outline in Scheme A.

Those compounds of formula I wherein $R^1$ and Z are both hydrogen and X and Y are the same may be prepared by the sequence of reactions represented by steps (k) and (m) of Scheme A. In step (k) a 2-halopropionic ester (II) is reacted with a tetrazole of formula $R^2H$ to give a 2-(2H-tetrazolyl)propionic ester (III) which is further reacted in step (m) with two molar equivalents of a 4-X-phenylmagnesium halide (such as the bromide or chloride) under the conditions of the Grignard Reaction to yield the compound of formula I.

The compounds of formula I may also be prepared by the sequence of reactions represented by steps (a), (b) and (c) in Scheme A. In step (a) the 2-halopropionic ester (II) is reacted with one molar equivalents of a substituted phenyl magnesium halide of formula:

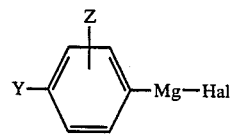

(wherein "hal" represents halogen, such as chlorine or bromine) to yield the α-halopropiophenone (IV) which is then reacted in step (b) with a tetrazole of formula $R^2H$ to give a α-(tetrazolyl)propiophenone (VII). This is converted into the compound of formula I by reaction in step (c) with a molar equivalent of the 4-X-phenylmagnesium halide. Alternatively, the similar procedure set out in Scheme A as steps (d), (e) and (f) may be used in which the 4-X-phenylmagnesium halide is reacted in step (d) with the 2-halopropionic ester to give the α-halopropiophenone (VI) which on reaction with the tetrazole in step (e) is converted to the α-(tetrazole)-propiophenone (VIII). This latter compound is then reacted in step (b) with the substituted phenylmagnesium halide (IX) to give the compound of formula I.

In another process outlined in steps (g) and (j) in Scheme A the α-halopropiophenone (IV) is reacted with the 4-X-phenylmagnesium halide to give the oxirane (V), which is converted to the compound of formula I by reaction with a tetrazole of formula R²H. The oxirane (V) may also be obtained by step (h) by reaction of a α-halopropiophenone (VI) with the substituted phenylmagnesium halide (IX).

The compounds of formula I wherein R¹ is hydrogen may be converted to the compounds of formula I wherein R¹ is alkyl by reaction with an appropriate alkyl halide in the presence of a base, and to compounds of formula I wherein R¹ is a carboxylic acyl group by reaction with an appropriate acyl halide of formula R¹CO—hal, such as the chloride, or an acid anhydride of formula (R¹CO)₂O.

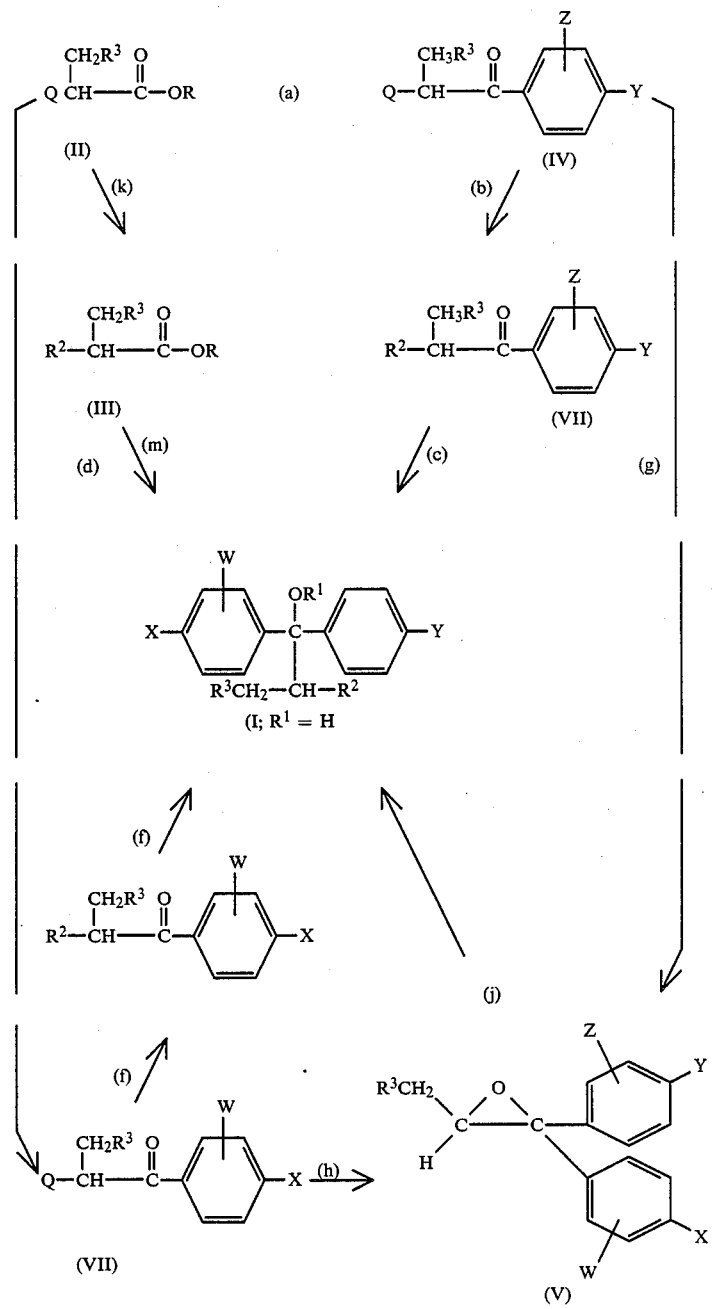

In Scheme A Q represents a suitable leaving group such as tosyloxy or halogen, preferably bromo or chloro, R is alkyl of up to 4 carbon atoms, and R², W, X, Y and Z have any of the meanings given hereinabove.

Many of the compounds of formula (III), (VII) and (VIII) are believed to be novel and in a further aspect therefore the invention provides:

(i) A compound of formula:

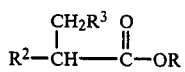

wherein $R^2$ is a tetrazolyl group, $R^3$ is hydrogen or alkyl and R is an alkyl group of up to 4 carbon atoms;

(ii) A compound of formula:

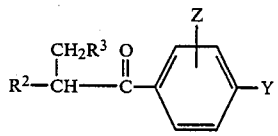

or formula

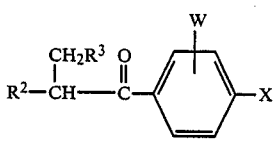

wherein X and Y are each selected from halo, difluoromethyl, trifluoromethyl, difluoromethoxy and trifluoromethoxy, W and X are each selected from hydrogen and halogen, $R^2$ is a tetrazolyl group, and $R^3$ is hydrogen or alkyl.

Specific compounds of formula III include
methyl 2-(2H-tetrazol-2-yl)propionate,
ethyl 2-(2H-tetrazol-2-l)propionate,
methyl 2-(1H-tetrazol-1-yl)propionate, and
ethyl 2-(1H-tetrazol-1-yl)propionate.
methyl 2-(2H-tetrazol-2-yl)butyrate
methyl 2-(1H-tetrazol-1-yl)butyrate Specific compounds of formula VII or formula VIII include
4-fluoro-α-(2H-tetrazol-2-yl)propiophenone,
4-chloro-α-(2H-tetrazol-2-yl)propiophenone,
4-trifluoromethyl-α-(2H-tetrazol-2-yl)propiophenone,
4-trifluoromethoxy-α-(2H-tetrazol-2-yl)propiophenone,
3,4-difluoro-α-(2H-tetrazol-2-yl)propiophenone, and
4-trifluoromethoxy-α-(2H-tetrazol-1-yl)propiophenone.

Certain of the invention compounds where at least one of X and Y represents a halogalkoxy group may be prepared by reacting a bromohaloalkane or iodohaloalkane with the compound of formula I where at least one of X and Y is hydroxy. These latter compounds although not active as insecticides are useful intermediates for making insecticidal compounds of formula I. They may be prepared by the Grignard reaction between a halobenzene bearing a protected hydroxy group eg. a trialkylsilyloxy group and the compound of formula III, and thereafter removing the protecting group by eg. acid hydrolysis.

In a further aspect therefore the invention provides the compound of formula I wherein W, X, Y, Z, $R^2$ and $R^3$ have any of the meanings given hereinbefore, except that at least one of X and Y is hydroxy, and $R^1$ is hydrogen. A particularly preferred compund within this group is 1,1-bis(4-hyroxyphenyl)-2-(2H-tetrazol-2-yl)propanol.

The compounds of formula I may be used to combat and control infestations of insect pests and also other invertebrate pests, in particular, acarine pests. The insect and acarine pests which may be combated and controlled by the use of the invention compounds include those pests associated with agriculture (which term includes the growing of crops for food and fibre products, horticulture and animal husbandry), forestry, the storage of products of vegetable origin, such as fruit, grain and timber, and also those pests associated with the transmission of diseases of man and animals.

In order to apply the compounds to the locus of the pests they are usually formulated into compositions which include in addition to the insecticidally active ingredient of ingredients of formula I suitable inert diluent or carrier materials, and/or surface active agents. The compositions may also comprise another pesticidal material, for example another insecticide or acaricide, or a fungicide, or may also comprise a insecticide synergist, such as for example dodecyl imidazole, safroxan, or piperonyl butoxide.

The compositions may be in the form of dusting powders wherein the active ingredient is mixed with a solid diluent or carrier, for example kaolin, bentonite, kieselguhr, or talc, or they may be in the form of granules, wherein the active ingredient is absorbed in a porous granular material for example pumice.

Alternatively the compositions may be in the form of liquid preparations to be used as dips or sprays, which are generally aqueous dispersions or emulsions of the active ingredient in the presence of one or more known wetting agents, dispersing agents or emulsifying agents (surface active agents).

Wetting agents, dispersing agents and emulsifying agents may be of the cationic, anionic or non-ionic type. Suitable agents of the cationic type include, for example, quaternary ammonium compounds, for example cetyltrimethyl ammonium bromide. Suitable agents of the anionic type include, for example, soaps, salts of aliphatic monoesters of sulphuric acid, for example sodium lauryl sulphate, salts of sulphonated aromatic compounds, for example sodium dodecylbenzenesulphonate, sodium, calcium or ammonium lignosulphonate, or butylnaphthalene sulphonate, and a mixture of the sodium salts of diisopropyl- and triisopropylnaphthalene sulphonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

The compositions may be prepared by dissolving the active ingredient in a suitable solvent, for example, a ketonic solvent such as diacetone alcohol, or an aromatic solvent such as trimethylbenzene and adding the mixture so obtained to water which may contain one or more known wetting, dispersing or emulsifying agents. Other suitable organic solvents are dimethyl formamide, ethylene dichloride, isopropyl alcohol, propylene glycol and other glycols, diacetone alcohol, toluene, kerosene, white oil, methylnaphthalene, xylenes and trichloroethylene, N-methyl-2-pyrrolidone and tetrahydro furfuryl alcohol (THFA).

The compositions to be used as sprays may also be in the form of aerosols wherein the formulation is held in a container under pressure in the presence of a propellant such as fluorotrichloromethane or dichlorodifluoromethane.

The compositions which are to be used in the form of aqueous dispersions or emulsions are generally supplied in the form of a concentrate containing a high proportion of the active ingredient or ingredients, the said concentrate to be diluted with water before use. These concentrates are often required to withstand storage for prolonged periods and after such storage, to be capable of dilution with water to form aqueous preparations which remain homogenous for a sufficient time to enable them to be applied by conventional spray equipment. The concentrates may contain 10–85% by weight of the active ingredient or ingredients. When diluted to form aqueous preparations such preparations may contain varying amounts of the active ingredient depending upon the purpose for which they are to be used. For agricultural or horticultural purposes, an aqueous preparation containing between 0.0001% and 0.1% by weight of the active ingredient is particularly useful.

In use the compositions are applied to the pests, to the locus of the pests, to the habitat of the pests, or to growing plants liable to infestation by the pests, by any of the known means of applying pesticidal compositions, for example, by dusting or spraying.

The compositions of the invention are very toxic to wide varieties of insect and other invertebrate pests, including, for example, the following:

*Aphis fabae* (aphids)
*Megoura viceae* (aphids)
*Musca domestica* (houseflies)
*Plutella xylostella* (diamond back month, larvae)
*Tetranychus cinnabarinus* (carmine spider mite)
*Tetranychus urticae* (red spider mites)
*Panonychus ulmi* (citrus rust mite)
*Trialeuroides spp.* (white flies)
*Diabrotica spp.* (rootworms)
*Heliothis virescens* (tobacco budworm)
*Blatella germanica* (cockroaches)

The various aspects of the invention are illustrated by the following Examples.

EXAMPLE 1

This Example illustrates the preparation of methyl 2-(1H-tetrazol-1-yl)propionate and methyl 2-(2H-tetrazol-2-yl)propionate.

A mixture of methyl 2-bromopropionate (66.8 g), tetrazole (28.02 g), potassium carbonate (110.4 g) and dry acetone (1.01) was heated at the reflux temperature for 4 hours and then cooled to the ambient temperature (ca. 22° C.). The solid component was removed by filtration and the filtrate concentrated under reduced pressure to give a yellow oil (60 g) which was subjected to distillation under reduced pressure to yield methyl 2-(2H-tetrazol-2-yl)-propionate as a colourless oil (18.0 g) b.p. 88°–93° C./1.5–2.5 mmHg.

Nmr (CDCl$_3$) δ: 2.0 (d, 3H); 3.8 (s, 3H); 5.72 (q, 1H); 8.6 (s, 1H). Infra red (liquid film): 1750 cm$^{-1}$.

The material remaining undistilled under these conditions was decolorised passing through a short column of silica gel to give methyl 2-(1H-tetrazol-1-yl)-propionate as a colourless oil (35 g, 99% pure by gas liquid chromatographic analysis).

Nmr (CDCl$_3$) δ: 1.95 (d, 3H); 3.8 (s, 3H); 5.58 (q, 1H); 8.95 (s, 1H).

EXAMPLE 2

By a procedure similar to that illustrated in the previous example the following compounds were obtained from the appropriate bromo ester. (i) ethyl 2-(2H-tetrazol-2-yl)propionate (colourless oil).

Nmr (CDCl$_3$) δ: 1.24 (t, 3H); 2.0 (d, 3H); 4.2 (q, 2H); 5.73 (q, 1H); 8.59 (s, 1H). (ii) ethyl 2-(1H-tetrazol-1-yl)propionate (solid).

Nmr (CDCl$_3$) δ: 1.29 (t, 3H); 1.94 (d, 3H); 4.26 (q, 2H); 5.60 (q, 1H); 8.97 (s, 1H). (iii) methyl 2-(2H-tetrazol-2-yl)butyrate.

Nmr (CDCl$_3$) δ: 0.94 (t, 3H); 2.48 (m, 2H); 3.78 (s, 3H); 5.74 (m, 1H); 8.62 (s, 1H). (iv) methyl 2-(1H-tetrazol-1-yl)butyrate.

Nmr (CDCl$_3$) δ: 0.95 (t, 3H); 2.3 (m, 2H); 3.82 (s, 3H); 5.45 (dd, 1H); 9.0 (s, 1H).

EXAMPLE 3

This Example illustrates the preparation of 1,1-bis(4-trifluoromethylphenyl)-2-(2H-tetrazol-2-yl)propanol (Compound no VII, Table I).

A few cm$^3$ of a solution of 4-bromobenzotrifluoride (5.8 g) in dry tetrahydrofuran (40 cm$^3$) was added slowly to a slowly stirred mixture of dry magnesium turnings (0.62 g) and dry tetrahydrofuran (to which had been added a single iodine crystal) at the ambient temperature under a nitrogen atmosphere. After a few minutes the reaction commenced, and the remainder of the 4-bromobenzotrifluoride solution was added slowly over a period until all the magnesium had been consumed. After stirring the resultant red solution at the ambient temperature for 2 hours a concentrated solution of methyl 2-(2-2H-triazolyl)propionate (2.0 g) in dry tetrahydrofuran (2.0 cm$^3$) was added slowly and the resultant mixture stirred for 2 hours at the ambient temperature, and then for 3 hours at 40° C. After adding water the mixture was acidified with dilute hydrochloric acid and extracted with diethyl ether (2×50 cm$^3$). The extracts were combined, washed three times with water and dried over anhydrous magnesium sulphate. After removal of the ether by evaporation under reduced pressure the residual oil (2.0 g) was purified by preparative h.p.l.c. (Gilson) using a silica column and a mixture of dichloromethane and ethyl acetate (3:2 by volume) to yield 1,1-bis(4-trifluoromethylphenyl) 2-(2H-tetrazol-2-yl)propanol (760 mg).

Nmr. (CDCl$_3$)δ: 1.59 (d, 3H); 4.95(s, 1H); 6.23 (q, 1H); 7.68 (m, 8H); 8.4 (s, 1H). Infra red (liquid film): 3500 cm$^{-1}$

EXAMPLE 4

This Example illustrates the preparation of 1,1-bis(4-trifluoromethoxyphenyl)-2-(2H-tetrazol-2-yl)propanol (compound no. IX, Table I).

A proportion (ca. 25 cm$^3$) of a solution of 4-bromotrifluoromethoxybenzene (45.79 g) in dry tetrahydrofuran (200 cm$^3$) was added to a gently stirred mixture of magnesium turnings (4.56 g) and dry tetrahydrofuran and a crystal of iodine under a nitrogen atmosphere. When the exothermic reaction had commenced the temperature of the mixture was maintained at the reflux temperature by the careful addition of the remaining 4-bromotrifluorobenzene followed by heating the mixture for a further hour at the reflux temperature. The mixture was cooled to the ambient temperature and stirred under a nitrogen atmosphere whilst a solution of methyl 2-(2H-tetrazol-2-yl)propionate (13.95 g) in dry tetrahydrofuran (60 cm³) was added dropwise, followed by heating the mixture at the reflux temperature for 30 minutes. The mixture was cooled and poured into water (500 cm³) and the resultant mixture acidified with 2N hydrochloric acid (250 cm³) and extracted with diethylether (3×400 cm³). The extracts were combined, dried over anhydrous magnesium sulphate and concentrated by evaporation of the solvents under reduced pressure to give a residual oil (30.5 g). This was subjected to purification by chromatography on a silica gel column using a mixture of n-hexane (4 parts by volume) and ethyl acetate (1 part by volume), and thereafter by h.p.l.c. of the fractions containing the product using the same eluant, to yield 1,1-bis(4-trifluoromethoxyphenyl)-2-(2H-tetrazol-2-yl)propanol (10.0 g), which crystallised on standing to a white solid, m.p. 68°–70° C.

Nmr (CDCl₃) δ: 1.55 (d, 3H); 4.8 (s, 1H); 6.1 (q, 1H); 7.4 (m, 8H); 8.4 (s, 1H).

EXAMPLE 5

By the use of procedures similar to those illustrated in Examples 3 and 4 the following compounds were prepared from the appropriate reactants. (i) 1,1-bis(4-trifluoromethylphenyl)-2-(1H-tetrazol-1-yl)propanol (compound no. VI, Table I) from 4-bromobenzotrifluoride and methyl 2-(1H-tetrazolyl)propionate.

(ii) 1,1-bis(4-fluorophenyl)-2-(2H-tetrazol-2-yl)-propanol (compound no. 1, Table I) from 4-bromofluorobenzene and methyl 2-(2H-tetrazol-2-yl)-propionate.

¹H Nmr (CDCl₃) δ: 1.53 (d, 3H); 4.71 (s, 1H); 6.14 (q, 1H); 6.7–7.6 (m, 8H); 8.38 (s, 1H).

(iii) 1,1-bis(3,4-difluorophenyl)-2-(2H-tetrazol-2-yl)-propanol (compound no. II, Table I) from 3,4-di-fluorobromobenzene and methyl 2-(2H-tetrazol-2-yl)propionate.

¹H Nmr (CDCl₃) δ: 1.55 (d, 3H); 4.85 (s, 1H); 6.07 (q, 1H); 6.8–7.6 (m, 6H); 8.4 (s, 1H).

(iv) 1,1-bis(4-chlorophenyl)-2-(2H-tetrazol-2-yl)propanol (compound no. III, Table I) from 4-chloroiodobenzene and methyl 2-(2H-tetrazol-2-yl)propionate.

¹H Nmr (CDCl₃) δ: 1.53 (d, 3H); 4.76 (s, 1H); 6.12 (q, 1H); 7.1–7.6 (m, 8H); 8.38 (s, 1H).

(v) 1,1-bis(4-trifluoromethoxyphenyl-2-(2H-tetrazol-2-yl)butanol (compound no. XIII, Table I) from 4-bromotrifluoromethoxybenzene and methyl 2-(2H-tetrazol-2-yl)butyrate.

¹H Nmr (CDCl₃) δ: 0.87 (t, 3H); 1.5–2.4 (m, 2H); 4.78 (s, 1H); 5.9 (dd, 1H); 7.0–7.7 (m, 8H); 8.41 (s, 1H).

EXAMPLE 6

This Example illustrates the preparation of 1,1-bis-[4-(1,1,2,2-tetrafluoroethoxy)phenyl]-2-(2H-tetrazol-2-yl)propanol (compound no. XV, Table I) and 1-[(1,1,2,2-tetrafluoroethoxy)phenyl]-1-[4-(1,2,2-trifluorovinyloxy)-phenyl]-2-(2H-tetrazol-2-yl)propanol (compound no. XVII, Table I).

A solution of 4-bromo-(1,1,2,2-tetrafluoroethoxy)-benzene (16.38 g) in dry tetrahydrofuran (60 cm³) was added quickly to a stirred mixture of magnesium turnings (1.46 g), dry tetrahydrofuran (20 cm³) and a crystal of iodine under a nitrogen atmosphere in a glass reaction vessel which was held in an ultrasonic bath. After 2 hours it was observed that most of the magnesium had reacted and a solution of ethyl 2-(2H-tetrazol-2-yl)-propionate (5.11 g) in dry tetrahydrofuran (25 cm³) was added to the stirred mixture, after which the mixture was heated at the reflux temperature for 2.5 hours. After cooling to the ambient temperature the mixture was poured into water (150 cm³) and the resultant mixture acidified with 3N aqueous hydrochloric acid (100 cm³), followed by extraction with diethyl ether (3×150 cm³). The extracts were combined, dried over anhydrous magnesium sulphate and concentrated by evaporation of the solvents. Examination of the residual oil by gas liquid chromatography showed that three products (retentin times 8.51, 8.77 and 8.89 minutes) were present in addition to some of the starting materials. The three products were identified by gas chromatographic mass spectroscopy as 1,1-bis[4-(1,2,2-trifluorovinyloxy)-phenyl]-2-(2H-tetrazol-2-yl)propanol, 1-[4-(1,1,2,2-tetrafluoroethoxy)phenyl]-1-[4-1,2,2-trifluorovinyloxy)-phenyl]-2-(2H-tetrazol-2-yl)propanol and 1,1-bis[4-(1,1,2,2-tetrafluorovinyloxy)phenyl]-2-(2H-tetrazol-2-yl)propanol respectively in the approximate ratio 1:2:2 (by weight). After removal of the starting materials by distillation up to a bath temperature of 140° C. at 1 mmHg, the residual oil was subjected to h.p.l.c. using a silica column eluted with a mixture of n-hexane (4 parts by volume) and ethylacetate (1 part by volume) to yield two of the three components in a pure state, identified as follows.

(i) 1,1-bis[4-(1,1,2,2-tetrafluoroethoxy)phenyl]-2-(2H-tetrazol-2-yl)propanol (0.33 g), colourless oil.

¹H Nmr (CDCl₃) δ: 1.56 (d, 3H); 4.80(s, 1H); 5.9 (complex, 2H); 6.16 (q, 1H); 7.0–7.7 (m, 8H); 8.4 (s, 1H).

(ii) 1-[4-(1,1,2,2-tetrafluoroethoxy)phenyl]-1-[4-(1,2,2-trifluoroethoxy)phenyl]-2-(2H-tetrazol-2-yl)propanol, colourless oil.

¹H nmr (CDCl₃) δ: 1.56 (d, 3H); 4.78 (S, 1H); 5.9 (complex, 1H); 6.15 (q, 1H); 6.8–7.6 (m, 8H); 8.4 (S 1H).

EXAMPLE 7

By the use of a procedure similar to that illustrated in Example 6 1,1-bis(4-bromophenyl)-2-(2H-tetrazol-2-yl)propanol (Compound No. IV, Table I) was obtained from 1,4-dibromobenzene and methyl 2-(2H-tetrazol-2-yl)propionate. Under the reaction condition a complex mixture of products was obtained by an initial chromatographic treatment using a silica gel column eluted with an n-hexane/ethyl acotate mixture (4:1 parts by volume). This contained the required product along with 1-(4-bromophenyl)-1-phenyl-2-(2H-tetrazol-2-yl)propanol and 1,1-diphenyl-2-(2H-tetrazol-2-yl)propanol in the ratio 58:33:9 by weight. The mixture of these three components was subject to reverse phase h.p.l.c by elution with an acetonitrile/water mixture (3:2 parts by volume) on a Waters C-18 support to obtain, in a pure state 1,1-bis(4-bromophenyl)-2-(2H-tetrazol-2-yl)propanol.

¹H nmr (CDCl₃) δ: 1.55 (d, 3H); 4.75 (S, 1H); 6.13 (q, 1H); 7.3–7.5 (m, 8H); 8.40 (S, 1H).

EXAMPLE 8

This Example illustrates the preparation of 1,1-bis(4-difluoromethoxyphenyl)-2-(2H-tetrazol-2-yl)propanol (compound no XIV, Table I).

(a) Preparation of 4-bromo-1-(t-butyldimethylsilyloxy)benzene.

Imidazole (28.46 g) was added to a stirred mixture of 4-bromophenol (32.87 g), t-butyldimethylsilylchloride (3.15 g) and dry dimethyl formamide (150 cm³) at the ambient temperature and the mixture stirred for a further 6 hours. The mixture was pored into 5% aqueous sodium bicarbonate solution (750 cm³) and extracted with diethyl ether (3×200 cm³), the extracts combined and dried over anhydrous magnesium sulphate and concentrated by evaporation of the solvents to yield a yellow oil (56.3 g). This was purified by eluting throught a silica column with a mixture of n-hexane and ethyl ecetate (3:1 by volume) to yield 4-bromo-1-(t-butyl dismethylsilyloxy)benzene (55.0 g, 97% pure by g.l.c).

(b) Preparation of 1,1-bis[4-(t-butyldimethylsilyloxy)-phenyl]-2-(2H-tetrazol-2-yl)propanol.

A procedure similar to that of Example 6 was used except that the reaction mixture was poured into iced saturated ammonium chloride solution and the product extracted into diethyl ether, thus avoiding strongly acidic conditions. The product was purified by h.p.l.c (silica gel column eluted with an n-hexane/ethyl acetate (4:1 by volume) mixture) to give 1,1 bis-[4-(t-butyldimethylsilyloxy)phenyl]-2-(2H-tetrazol-2-yl)propanol as a colourless solid.

$^1$H n.m.r (CDCl$_3$) δ: 0.1, 0.2 (2s, 12H); 0.9 (2s, 18H); 1.55 (d, 3H); 4.53 (s, 1H); 6.1 (q, 1H); 6.6–7.5 (m, 8H); 8.4 (s, 1H)

Infra red (liquid paraffin): 3510, 1615, 1510, 1270, 1180, 925, 845 cm$^{-1}$.

(c) Preparation of 1,1-bis(4-hydroxyphenyl)-2-(2H-tetrazol-2-yl)propanol.

A mixture of 1,1-bis[4-[4-(t-butyldimethylsilyloxy)-phenyl]-2-(2H-tetrazol-2-yl)propanol (1.08 g), glaial acetic acid (40 cm$^3$), methanol (20 cm$^3$) and water (20 cm$^3$) was heated at 95° C. for 6.5 hours, cooled to the ambient temperature, and extracted with ethyl acetate (50 cm$^3$). The organic phase was separated, washed with water (50 cm$^3$), saturated sodium bicarbonate solution (3×50 cm$^3$) and water (2×30 cm$^3$). After drying the extracts over anhydrous magnesium sulphate this solvent was removed by evaporation under reduced pressure and this residual solid recrystallised from a mixture of ethyl acetate and n-hexane to give 1,1-bis(4-hydroxyphenyl)-2-(2H-tetrazol-2-yl)propanol (0.35 g) as a white solid.

$^1$H n.m.r (CD$_3$OD) δ: 1.6 (d, 3H); 6.2 (q, 1H); 6.5–7.6 (m, 8H); 8.53 (s, 1H).

(d) Preparation of 1,1-bis(4-difluoromethoxyphenyl)-2-(2H-tetrazol-2-yl)propanol (Compund no XIV, Table I).

Gaseous bromodifluoromethane was passed into a vigorously stirred mixture of 1,1-bis(4-hydroxyphenyl)-2-(2H-tetrazol-2-yl)propanol (0.23 g), tetrahydrofuran (3.0 cm$^3$) and an aqueous solution of sodium hydroxide (0.32 g) in water (2.5 cm$^3$) held at 65° C. over a period of three hours. The resultant mixture was diluted with water (30 cm$^3$) and extracted with diethyl ether (3×20 cm$^3$), the ethereal extracts combined, dried over anhydrous magnesium sulphate and concentrated by evaporation of the solvent to give a brown oil. This was subjected to preparative h.p.l.c on a silica gel column using, as eluant, a mixture of ethyl acetate and n-hexane (2:3 by volume) to yield 1,1-bis(4-difluoromethoxyphenyl)-2-(2H-tetrazol-2-yl)propanol (29 mg).

$^1$H n.m.r (CDCl$_3$) δ: 1.55 (d, 3H); 4.73 (S, 1H); 6.15 (q, 1h); 6.4, 6.5 (2t, 2H); 6.9–7.6 (m, 8H); 8.4 (S, 1H).

EXAMPLE 9

This Example illustrates the preparation of 4-chloro-1-[2-oxo-3-(2H-tetrazol-2-yl)propyl]benzene and 4-chloro-1-[2-oxo-3-(1H-tetrazol-1-yl)propyl]benzene.

A mixture of tetrazole (5.0 g), 4-chloro-1-(2-oxo-3-bromopropyl)benzene (15.0 g), potassium, carbonate (10.0 g) and acetonitrile (50 cm$^3$) was heated at 60° C. for 40 minutes, poured in water, and extracted with ethyl acetate. The extracts were washed with water, dried over anhdrous magnesium sulphate and concentrated by evaporation of the solvent to give a residual solid (14.0 g). This material was eluted through a silica gel column with a mixture of ethyl acetate and n-hexane (3:7 by volume) to yield a first product which was recrystallised from a mixture of chloroformate and n-hexane (2.5 g), identified as 4-chloro-1-[2-oxo-3-(2H-tetrazol-2-yl)propyl]benzene.

$^1$H n.m.r δ: 2.0 (d, 3H); 6.9 (q, 1H); 7.5–8.1 (m, 4H); 8.78 (s, 1H).

Further elution of the column with a chloroform/methanol mixture (19:1 by volume) yielded a second product, which was recrystallised from a chloroform and n-hexane mixture, (2.35 g) identified as 4-chloro-1-[2-oxo-3-(1H-tetrazol-1-yl)propyl]benzene.

$^1$H n.m.r (CDCl$_3$) δ: 1.97 (d, 3H); 6.8 (q, 1H); 7.5–8.2 (m, 4H); 9.47 (s, 1H).

EXAMPLE 10

By the use of a similar procedure to that illustrated in Example 9, except that acetone was used in place of acetonitrile, the following products were identified from the reaction of tetrazol with 4-ethoxy-1-(2-oxo-3-bromopropyl)benzene. (i) 4-ethoxy-1-[2-oxo-3-(2H-tetrazol-2-yl)propyl]benzene $^1$H n.m.r. (CDCl$_3$) δ: 1.44 (t, 3H); 2.03 (d, 3H); 4.11 (q, 2H); 6.55 (q, 1H); 6.95, 7,92 (2m, 4H); 8.55 (s, 1H). (ii) 4-ethoxy-1-[2-oxo-3-(1H-tetrazol-1-yl)propyl]benzene.

$^1$H n.m.r. (CDCl$_3$) δ: 1.45 (t, 3H); 1.9 (d, 3H); 4.13 (q, 2H); 6.56 (q, 1H); 7.0, 8.0 (2m, 4H); 8.96 (S, 1H).

EXAMPLE 11

This Example illustrates the preparation of 1-(4-chlorophenyl)-1-(4-trifluoromethylphenyl)-2-(2H-tetrazol-2-yl)propanol (compound no V, Table I).

4-Bromobenzotrifluoride (1.8 g) was added slowly to a stirred mixture of magnesium turnings (0.2 g) and tetrahydrofuran (6.0 cm$^3$) in the presence of a small crystal of iodine under a nitrogen to yield a solution of 4-trifluoromethyl phenyl magnesium bromide. To this was added a solution of 4-chloro-1-[2-oxo-3-(2H-tetrazol-2-yl)propyl]benzene (1.9 g) in tetrahydrofuran (6.0 cm$^3$) and this resultant mixture stirred for 2 hours at this ambient temperature, and then at the reflux temperature for 30 minutes. The mixture was cooled, poured in water (30 cm$^3$), and acidified with 3N hydrochloric acid (30 cm$^3$), and extracted with diethyl ether (3×40 cm$^3$). The extracts were combined, dried over anhydrous magnesium sulphate, and concentrated by evaporation of the solvent. The residual oil (3.3 g) was subjected to purification by h.p.l.c using a silica gel column and elution with a mixture of n-hexane and ethyl acetate (4:1 by volume) to yield 1-(4-chlorophenyl)-1-(4-trifluoromethylphenyl)-2-(2H-tetrazol-2-yl)propanol (2.8 g) as a colourless oil which crystallised on standing, mp 123°–125° C.

$^1$H n.m.r. (CDCl$_3$) δ: 1.55 (d, 3H); 4.85 (s, 1H); 6.18 (q, 1H); 7.2–7.7 (m, 8H); 8.38 (s, 1H).

EXAMPLE 12

By the use of a similar procedure to that illustrated in Example 11 the following compounds were also obtained from the appropriate reactants. (i) 1-(4-chlorophenyl)-1-(4-trifluoromethoxyphenyl)-2-(2H-tetrazol-2-yl)propanol (Compound no VIII, Table I) from 4- bromotrifluoromethoxybenzene and 4-chloro-1-[2-oxo-3-(2H-tetrazol-2-yl)propyl]benzene.

$^1$H n.m.r (CDCl$_3$) δ: 1.55 (d, 3H); 4.8 (s, 1H); 6.12 (q, 1H); 7.0 (m, 2H); 7.3–7.6 (m, 6H); 8.38 (s, 1H). (ii) 1-(4-ethoxyphenyl)-1-(4-trifluoromethoxyphenyl)-2-2H-tetrazol-2-yl)propanol (compound no XVII, Table I) from 4-bromotrifluoromethoxybenzene and 4-ethoxy-1-[2-oxo-3-(2H-tetrazol-2-yl)propyl]benzene.

$^1$H n.m.r (CDCl$_3$) δ: 1.2 (t, 3H); 4.03 (q, 2H); 4.7 (s, 1H); 6.13 (q, 1H); 6.8–7.6 (m, 8H); 8.38 (s, 1H).

EXAMPLE 13

This Example illustrates the preparation of 1,1-bis(4-trifluoromethoxyphenyl)-1-methoxy-2-(2H-tetrazol-21-yl)propane (compund no X, Table I).

1,1-bis(4-trifluoromethoxyphenyl)-2-(2H-tetrazol-2-yl)propanol (220 g) was added to a stirred suspension of sodium hydride (24 mg of a 50% dispension in oil) in dry dimethylformamide (6.0 cm$^3$) at the ambient temperature under a nitrogen atmosphere, and the mixture stirred for a further 2 hours after which methyl iodide (71 mg) was added and the resultant mixtures stirred for a further 20 hours. After diluting with water the mixture was extracted with diethyl ether (3×15 cm$^3$), the extracts were combined, dried over anhydrous magnesium sulphate and concentrated by evaporation of the solvent under reduced pressure. The residual yellow oil was subjected to h.p.l.c using a silica gel column eluted with a mixture of n-hexane and ethyl acetate (5:1 by volume) to yield 1,1-bis(4-trifluoromethoxyphenyl)-1-methoxy-2-(2H-tetrazol-2-yl)propane.

$^1$H n.m.r (CDCl$_3$/CD$_3$COOD) δ: 1.73 (d, 3H); 3.06 (s, 3H); 6.5 (q, 1H); 7.2–7.4 (m, 8H); 8.5 (s, 1H).

EXAMPLE 14

By the use of a procedure similar to that illustrated in Example 13 1,1-bis(4-trifluoromethoxyphenyl)-1-ethoxy-2-(2H-tetrazol-2-yl)propane (Compound no XI, Table I) was obtained from 1,1-bis(4-trifluoromethoxyphenyl)-2-(2H-tetrazol-2-yl)propanol and ethyl iodide).

$^1$H n.m.r (CDCl$_3$) δ: 1.06 (t, 3H); 1.68 (d, 3H); 2.7–3.4 (m, 2H); 6.16 (q, 1H); 9.2 (m, 8H); 8.34 (s, 1H).

EXAMPLE 15

By the use of a procedure similar to that illustrated in Example 13 except that acetyl chloride was used in place of methyl iodide there was obtained 1-acetoxy-1,1-bis(4-trifluoromethoxyphenyl)-2-(2H-tetrazol-2-yl)propane (Compound no XII, Table I).

$^1$H n.m.r (CDCl$_3$) δ: 1.80 (d, 3H); 2.03 (s, 3H); 6.89 (q, 1H); 7.0–7.4 (m, 8H); 8.4 (s, 1H).

EXAMPLE 16

The insecticidal activity of compounds according to the invention is set out in Table III as a grading of A, B or C where A indicates that 80–100% mortality was observed, B indicates that 50–79% mortality was observed and C indicates that 0–49% mortality was observed. The tests were conducted by supporting the test species on a medium (eg. leaves of a suitable food plant, or filter paper) and spraying the pests and medium (contact test-"CT" in Table II) or by spraying the medium before placing the pests thereon (residual test-"RT" in Table II). Assessment of mortality was made 72 hours after spraying except for houseflies (Musca domestica) where the assessment was made after 24 hours. In the test the compounds were used in the form of aqueous composition comprising 500 parts per million of the compound prepared by dissolving the compound in mixture of solvents consisting of 4 parts by volume by acetone and 1 part by volume of diacetone alchol and diluting the solution with water containing 0.01% by weight of a wetting agent ("Lissapol" NX-"Lissapol" is a Registered Trade Mark).

TABLE II

| CODE LETTERS (Table III) | TEST SPECIES | SUPPORT MEDIUM/FOOD | TYPE OF TEST | DURATION (days) |
|---|---|---|---|---|
| CP | Chilo partellus (maize stem borer) | Oil seed rape leaf | RT | 3 |
| HV | Heliothis viriscens (tobacco budworm) | Cotton leaf | RT | 3 |
| DB | Diabrotica balteata (rootworm larvae) | Filter paper/ maize seed | RT | 3 |
| BG | Blattella germanica (cockroach nymphs) | Plastic pot | RT | 3 |
| MD | Musca domestica (houseflies - adults) | Cotton wool/ sugar | CT | 1 |

TABLE III

| PRODUCT | MD | BG | HV | CP | DB |
|---|---|---|---|---|---|
| I | C | C | C | C | B |
| II | A | C | A | A | C |
| III | A | C | A | A | A |
| IV | A | C | B | A | C |
| V | A | B | A | A | A |
| VII | A | A | A | A | A |
| VIII | A | B | A | A | A |
| IX | A | A | A | A | A |
| X | A | A | A | A | A |
| XI | A | A | A | A | A |
| XII | C | C | A | C | — |
| XIII | C | A | A | C | A |
| XIV | A | C | A | A | A |
| XV | C | B | A | A | C |
| XVI | C | C | C | A | C |

"—" in Table III indicates not tested

I claim:
1. A compound of formula:

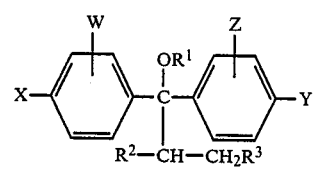

(I)

wherein X and Y are each selected from halo, alkyl of up to four carbon atoms, haloalkyl of up to four carbon atoms, alkoxy of up to four carbon atoms, haloalkoxy of up to four carbon atoms and haloalkenyloxy of up to four carbon atoms, provided that no more than one of X and Y is alkyl or alkoxy, and W and Z are each selected from hydrogen and halogen, R$^1$ is hydrogen, alkyl of up to 6 carbon atoms or alkyl CO- of up to 10 carbon atoms, R² is the 1H-tetrazol-1-yl or 2H-tetrazol-2-yl group and R³ is hydrogen or alkyl of up to four carbon atoms.

2. A compound according to claim 1 wherein X and Y are selected from halo, difluoromethyl, trifluoromethyl, difluoromethoxy, trifluoromethoxy, W and Z are both hydrogen, R² is the 2H-tetrazol-2-yl group and R¹ and R³ are both hydrogen.

3. The compound according to claim 1 which is 1,1-bis(4-trifluoromethylphenyl)-2-(2H-tetrazol-2-yl)propanol.

4. The compound according to claim 1 which is 1,1-bis(4-trifluoromethoxyphenyl)-2-(2H-tetrazol-2-yl)propanol.

5. A compound of formula:

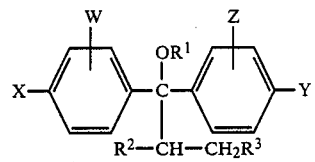

wherein R¹ is hydrogen, X and Y are each selected from hydroxy, halo, alkyl of up to four carbon atoms, haloalkyl of up to four carbon atoms, alkoxy of up to four carbon atoms, haloalkoxy of up to four carbon atoms and haloalkenyloxy of up to four carbon atoms, W and Z are each selected from hydrogen and halogen, R² is the 1H-tetrazol-1-yl or 2H-tetrazol-2-yl group and R³ is hydrogen or alkyl of up to four carbon atoms, at least one of X and Y being hydroxy.

6. The compound according to claim 5 which is 1,1-bis(4-hyroxyphenyl)-2-(2H-tetrazol-2-yl)propanol.

7. An insecticidal composition comprising an insecticidally effective amount of a compound according to claim 1 in association with an insecticidally inert agriculturally and horticulturally acceptable diluent or carrier.

8. A method of combating insect pests at a locus which comprises applying to the locus an insecticidally effective amount of a composition according to claim 4.

* * * * *